US008020447B2

(12) United States Patent
Okuda et al.

(10) Patent No.: US 8,020,447 B2
(45) Date of Patent: Sep. 20, 2011

(54) ULTRASONIC SENSOR AND SELF DIAGNOSTIC METHOD OF THE SAME

(75) Inventors: Yasuyuki Okuda, Aichi-gun (JP); Makiko Sugiura, Hekinan (JP)

(73) Assignee: DENSO CORPORATION, Kariya (JP)

( * ) Notice: Subject to any disclaimer, the term of this patent is extended or adjusted under 35 U.S.C. 154(b) by 497 days.

(21) Appl. No.: 12/153,823

(22) Filed: May 27, 2008

(65) Prior Publication Data

US 2009/0071255 A1 Mar. 19, 2009

(30) Foreign Application Priority Data

Jun. 12, 2007 (JP) ................................ 2007-155027

(51) Int. Cl.
*G01N 29/04* (2006.01)

(52) U.S. Cl. ........................................................ 73/628

(58) Field of Classification Search .................... 73/628, 73/632

See application file for complete search history.

(56) References Cited

U.S. PATENT DOCUMENTS

| | | | | |
|---|---|---|---|---|
| 7,329,975 | B2 | 2/2008 | Sugiura et al. | 310/334 |
| 7,522,475 | B2 * | 4/2009 | Kojima et al. | 367/188 |
| 2006/0043843 | A1 | 3/2006 | Sugiura et al. | 310/348 |
| 2006/0196272 | A1 | 9/2006 | Sugiura et al. | |
| 2007/0040477 | A1 | 2/2007 | Sugiura et al. | 310/324 |
| 2008/0116765 | A1 | 5/2008 | Sugiura et al. | 310/334 |

FOREIGN PATENT DOCUMENTS

| | | |
|---|---|---|
| JP | A-S63-149524 | 6/1988 |
| JP | A-H4-315082 | 11/1992 |
| JP | A-H7-327895 | 12/1995 |
| JP | A-11-178823 | 7/1999 |
| JP | A-2001-016694 | 1/2001 |
| JP | A-2003-284182 | 10/2003 |
| JP | A-2003-299195 | 10/2003 |
| JP | A-2005-233745 | 9/2005 |
| JP | A-2006-024256 | 1/2006 |
| JP | A-2006-270725 | 10/2006 |
| JP | A-2006-343309 | 12/2006 |

OTHER PUBLICATIONS

Office Action dated Jan. 26, 2009 in corresponding Japanese patent application No. 2007-155027 (and English translation).

Office Action dated May 12, 2009 from Japanese Patent Office in a corresponding Japanese application No. 2007-155027 (and English Translation).

* cited by examiner

*Primary Examiner* — Hezron E Williams
*Assistant Examiner* — Tamiko D Bellamy
(74) *Attorney, Agent, or Firm* — Posz Law Group, PLC

(57) ABSTRACT

In an ultrasonic sensor, a first receiving device is configured to be sendable and receivable an ultrasonic wave. The ultrasonic wave sent from the first receiving device is transmitted through a vibration-reducing member disposed between the first receiving device and a second receiving device, and the second receiving device detects the ultrasonic wave. The ultrasonic sensor self diagnoses whether the second receiving device is operated without malfunction based on a detection signal of the second receiving device.

11 Claims, 7 Drawing Sheets

ULTRASONIC SENSOR AND SELF DIAGNOSTIC METHOD OF THE SAME

CROSS REFERENCE TO RELATED APPLICATION

The present application is based on and claims priority to Japanese Patent Application No. 2007-155027 filed on Jun. 12, 2007, the contents of which are incorporated in their entirety herein by reference.

BACKGROUND OF THE INVENTION

1. Field of the Invention

The present invention relates to an ultrasonic sensor and a self diagnostic method of the ultrasonic sensor.

2. Description of the Related Art

Conventionally, an ultrasonic sensor includes an ultrasonic-wave detection element attached to a transmission member that transmits an ultrasonic wave. For example, the transmission member is made of metal or resin. The ultrasonic sensor sends an ultrasonic wave from a sending device and receives the ultrasonic wave reflected by an external object by using a receiving device. Thereby, the ultrasonic wave detects a location of the object, a distance to the object, a two-dimensional shape of the object, or a three-dimensional shape of the object. The ultrasonic sensor can be suitably used for a surveillance system of a vehicle. However, the ultrasonic sensor attached to the vehicle may be damaged by an external factor such as an impact. When the ultrasonic sensor is damaged, the surveillance system may malfunction and may be difficult to detect a people or an obstacle with a high degree of accuracy.

US 2006/0196272 A (corresponding to JP-2006-242650A) discloses a self diagnostic method of an ultrasonic sensor that includes a plurality of receiving devices. The ultrasonic sensor self-diagnoses based on a difference in intensity of detection signals of the receiving devices at a time where the receiving devices detect an ultrasonic wave reflected by an external object. Because the present self-diagnostic method uses the ultrasonic wave reflected by the external object, the ultrasonic sensor cannot detect a malfunction when there is no object in a range of detection. For example, when the vehicle is parked in a garage or parking space at which there is no object in front thereof, the ultrasonic sensor cannot detect a malfunction.

SUMMARY OF THE INVENTION

In view of the foregoing problems, it is an object of the present invention to provide a self diagnostic method of an ultrasonic sensor without using an ultrasonic wave reflected by an external object. Another object of the invention is to provide an ultrasonic sensor that can self-diagnose without using an ultrasonic wave reflected by an external object.

According to a first aspect of the invention, a self diagnostic method of an ultrasonic sensor includes: sending an ultrasonic wave from a first receiving device that is configured to be sendable and receivable; transmitting the ultrasonic wave through a vibration-reducing member; detecting the ultrasonic wave by a second receiving device; and determining whether the second receiving device is operated without malfunction based on a detection signal of the second receiving device. Each of the receiving devices includes a detecting element and an acoustic matching part. Each of the detecting elements has a first acoustic impedance and is configured to detect an ultrasonic wave that is sent from a sending device and that is reflected by an external object. Each of the acoustic matching parts has a second acoustic impedance and has a receiving surface and an attaching surface. Each of the receiving surfaces is exposed to an outside for detecting the ultrasonic wave reflected by the external object. Each of the attaching surfaces opposes the receiving surface and is attached to the detecting element for transmitting the ultrasonic wave received by the receiving surface to the detecting element. The second acoustic impedance is larger than an acoustic impedance of air and is less than the first acoustic impedance. The acoustic matching part of the first receiving device and the acoustic matching part of the second receiving device are arranged through the vibration-reducing member for reducing a transmission of a vibration between the acoustic matching parts.

In the present self diagnostic method, the ultrasonic sensor can detect a malfunction of the second receiving device without sending an ultrasonic wave toward the external object and detecting the ultrasonic wave reflected by the external object.

According to a second aspect of the invention, a self diagnostic method of an ultrasonic sensor includes: sending an ultrasonic wave from a first receiving device that is configured to be sendable and receivable; transmitting the ultrasonic wave through a sealing member; detecting the ultrasonic wave by a second receiving device; and determining whether the second receiving device malfunctions based on a detection signal of the second receiving device. Each of the receiving devices includes a detecting element and an acoustic matching part. Each of the detecting elements has a first acoustic impedance and is configured to detect an ultrasonic wave that is sent from a sending device and that is reflected by an external object. Each of the acoustic matching parts has a second acoustic impedance and has a receiving surface and an attaching surface. Each of the receiving surfaces is exposed to an outside for detecting the ultrasonic wave reflected by the external object. Each of the attaching surfaces opposes the receiving surface and is attached to the detecting element for transmitting the ultrasonic wave received by the receiving surface to the detecting element. The second acoustic impedance is larger than an acoustic impedance of air and is less than the first acoustic impedance. The acoustic matching part of the first receiving device and the acoustic matching device of the second receiving device are arranged through a vibration-reducing member for reducing a transmission of a vibration between the acoustic matching parts. The detecting element of the first receiving device and the detecting element of the second receiving device are sealed by the sealing member.

In the present self diagnostic method, the ultrasonic sensor can detect a malfunction of the second receiving device without sending an ultrasonic wave toward the external object and detecting the ultrasonic wave reflected by the external object.

According to a third aspect of the invention, a self diagnostic method of an ultrasonic sensor includes: sending an ultrasonic wave from a first sending device; detecting the ultrasonic wave by a plurality of receiving devices; and determining whether each of the receiving devices is operated without malfunction based on a detection signal of each of the receiving devices. Each of the receiving devices includes a detecting element and an acoustic matching part. Each of the detecting elements has a first acoustic impedance and is configured to detect an ultrasonic wave that is sent from a second sending device and that is reflected by an external object. Each of the acoustic matching parts has a second acoustic impedance and has a receiving surface and an attaching surface. Each of the receiving surfaces is exposed to an outside for detecting the ultrasonic wave reflected by the object. Each of the attaching surfaces opposes the receiving surface and is attached to the detecting element for transmitting the ultrasonic wave received by the receiving surface to the detecting element. Each of the second acoustic impedance is larger than an acoustic impedance of air and is less than the first acoustic impedance. The first sending device is disposed on a side of the detecting elements with respect to the receiving surfaces.

In the present self diagnostic method, the ultrasonic sensor can detect a malfunction of the receiving devices without sending an ultrasonic wave toward the external object and detecting the ultrasonic wave reflected by the external object.

According to a fourth aspect of the invention, an ultrasonic sensor includes a sending device, a first receiving device, a second receiving device, a vibration-reducing member, and an electronic control unit. The sending device is configured to send an ultrasonic wave toward an external object. The first receiving device is configured to be sendable an ultrasonic wave. Each of the first receiving device and the second receiving device includes a detecting element and an acoustic matching part. Each of the detecting elements has a first acoustic impedance and is configured to detect the ultrasonic wave that is sent from the sending device and that is reflected by the external object. Each of the acoustic matching parts has a second acoustic impedance and has a receiving surface and an attaching surface. Each of the receiving surfaces is exposed to the outside for detecting the ultrasonic wave reflected by the external object. Each of the attaching surfaces opposes the receiving surface and is attached to the detecting element for transmitting the ultrasonic wave received by the receiving surface to the detecting element. The second acoustic impedance is larger than an acoustic impedance of air and is less than the first acoustic impedance. The vibration-reducing member is disposed between the acoustic matching part of the first receiving device and the acoustic matching part of the second receiving device for reducing a transmission of a vibration between the acoustic matching parts. The determination unit for determining whether the second receiving device is operated without malfunction based on a detection signal of the second receiving device when the second receiving device detects the ultrasonic wave sent from the first receiving device through the vibration-reducing member.

The present ultrasonic sensor can detect a malfunction of the second receiving device without sending an ultrasonic wave toward the external object and detecting the ultrasonic wave reflected by the external object.

BRIEF DESCRIPTION OF THE DRAWINGS

Additional objects and advantages of the present invention will be more readily apparent from the following detailed description of preferred embodiments when taken together with the accompanying drawings. In the drawings.

DETAILED DESCRIPTION OF THE PREFERRED EMBODIMENTS

First Embodiment

Figure 1A:
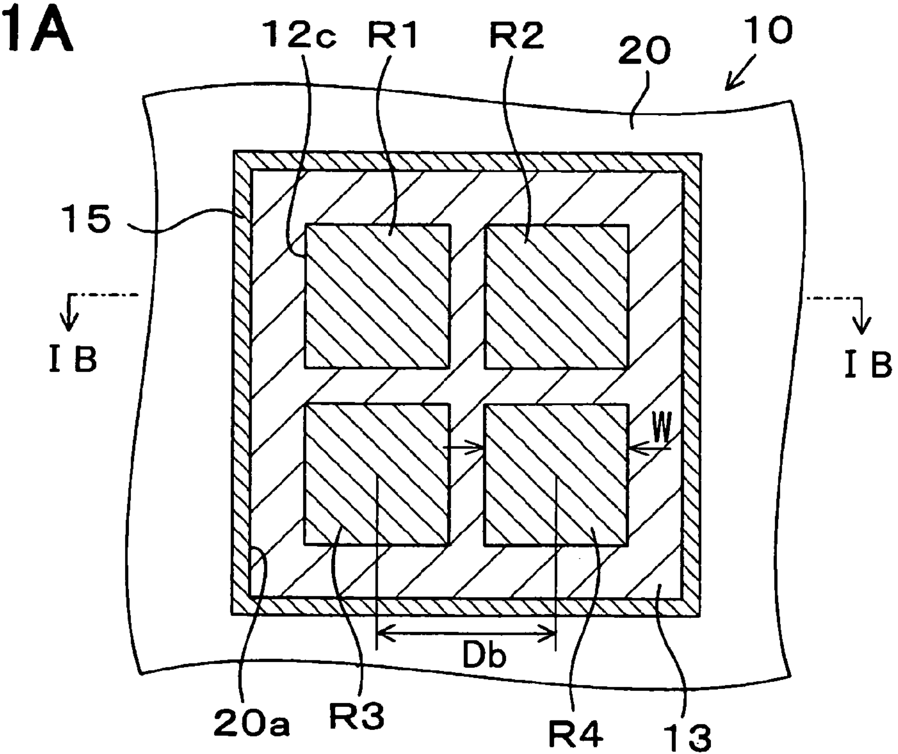
FIG. 1A is a plan view showing an ultrasonic sensor according to a first embodiment of the invention.

An ultrasonic sensor 10 according to a first embodiment of the invention will be described with reference to FIGS. 1A-5 and FIG. 9. For example, the ultrasonic sensor 10 can be suitably used as an obstacle sensor attached to a vehicle 60 shown in FIG. 9. In the present case, a front side in FIG. 1A and an upside in FIG. 1B correspond to an exterior of the vehicle 60. In addition, an up-and-down direction in FIG. 1A corresponds to an up-and-down direction with respect to a ground surface.

The ultrasonic sensor 10 includes first to fourth receiving devices R1-R4. Each of the receiving devices includes a piezoelectric element 11 and an acoustic matching part 12. The piezoelectric elements 11 detect an ultrasonic wave that is sent from sending device (not shown) toward a front side of the vehicle 60 and is reflected by an external object located in front of the vehicle 60. The acoustic matching parts 12 receive the ultrasonic wave and transmit a vibration. At least one of the receiving devices R1-R4 is sendable and receivable. In the present case, the first receiving device R1 is configured to be sendable and receivable, for example.

The second receiving device R2 is arranged on a right side of the first receiving device R1, the third receiving device R3 is arranged on a downside of the first receiving device R1, and the fourth receiving device R4 is arranged on a downside of the second receiving device R2, for example. Each of the acoustic matching parts 12 has a receiving surface 12*a* for receiving the ultrasonic wave, an attaching surface 12*b* opposing the receiving surface 12*a*, and side surfaces 12*c*. The ultrasonic sensor 10 further includes a casing 15 and a vibration-reducing member 13. The receiving devices R1-R4 are fixed at an opening portion of the casing 15 through the vibration-reducing member 13 by using an adhesive agent. Each portion of the side surfaces 12*c* on a side of the receiving surface 12*a* contacts the vibration-reducing member 13. The vibration-reducing member 13 reduces a transmission of the vibration among the receiving devices R1-R4.

Figure 1B:
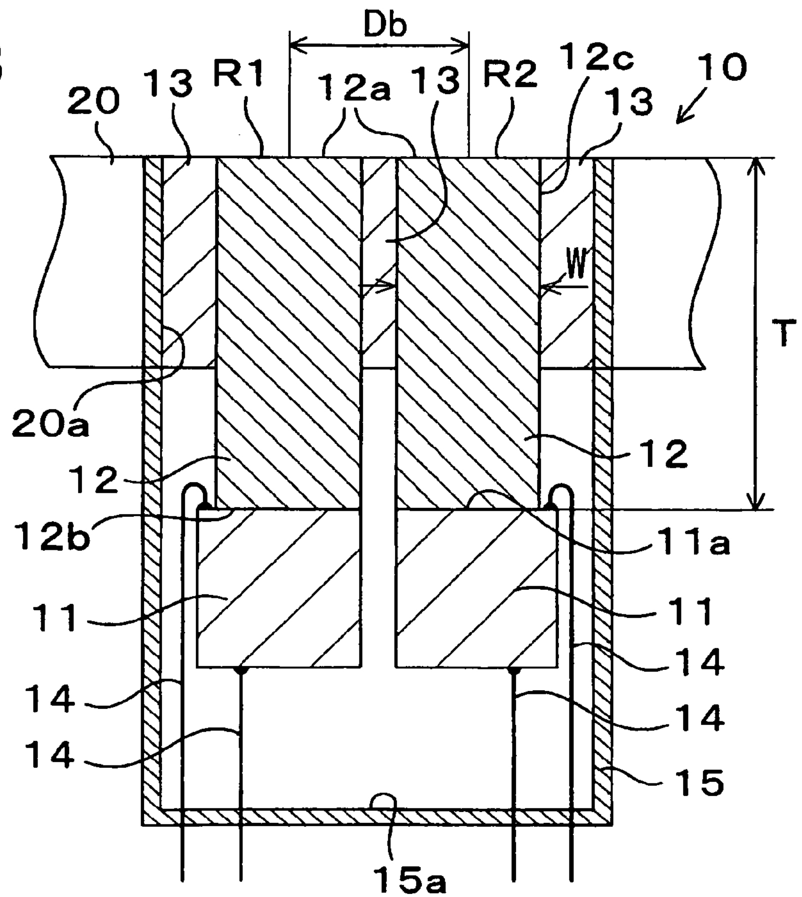
FIG. 1B is a cross-sectional view of the ultrasonic sensor taken along line IB-IB in FIG. 1A.
Figure 9:
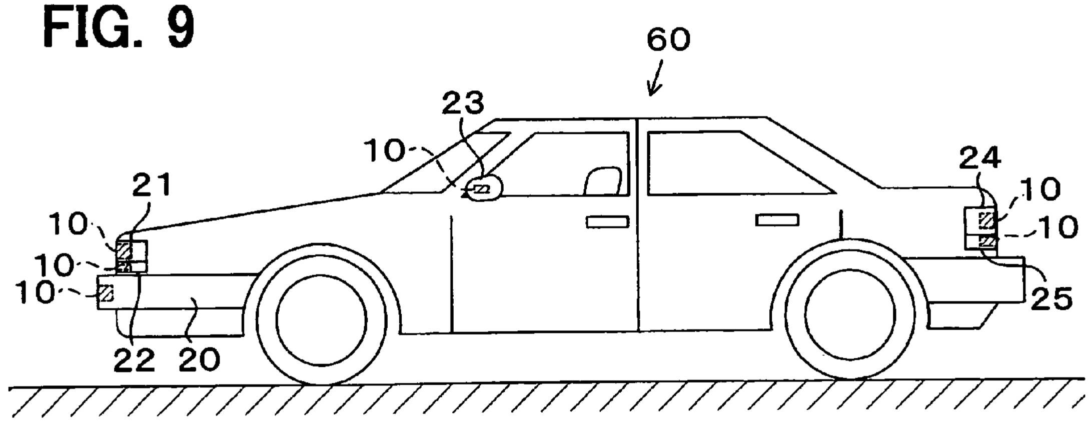
FIG. 9 is a schematic diagram showing exemplary portions of a vehicle at which the ultrasonic sensor is attached.

As shown in FIG. 1B and FIG. 9, the ultrasonic sensor 10 is attached to a predetermined portion of the vehicle 60, for example, a bumper 20. The bumper 20 has an attaching part 20*a* for housing the casing 15. A side surface of the casing 15 is attached to the attaching part 20*a* in such a manner that the receiving surfaces 12*a* are exposed to an outside of the bumper 20.

The piezoelectric elements 11 are attached to the attaching surfaces 12*b*, respectively, by an adhesives agent, for example. Each of the piezoelectric elements 11 has a substantially square prism shape with base edges of about 2 mm and a thick of about 3 mm. Each of the piezoelectric elements 11 has a piezoelectric body, and electrodes attached on an upper surface and a lower surface of the piezoelectric body. For example, the piezoelectric body is made of lead zirconate titanate (PZT). Each of the electrodes is electrically coupled with a circuit device (not shown) through a wire. The circuit device processes a voltage signal from the piezoelectric elements 11. The circuit device is electrically coupled with an electronic control unit (ECU) and executes arithmetic processing based on the voltage signal from the piezoelectric elements 11. Because the PZT has a large piezoelectric constant, the PZT can receive an ultrasonic wave having a small sound pressure.

Each of the acoustic matching parts 12 is made of a material that has an acoustic impedance larger than an acoustic impedance of air and less than an acoustic impedance of the piezoelectric elements 11. Each of the acoustic matching parts 12 has a prism shape having an approximately square cross-sectional shape. In a case where the acoustic matching parts 12 are provided, a difference in the acoustic impedance at an interface with respect to air can be reduced compared with a case where the acoustic matching parts 12 are not provided. That is, the difference in the acoustic impedance between air and the acoustic matching parts 12 is less than the difference in the acoustic impedance between air and the piezoelectric elements 11. Thus, the receiving devices R1-R4 can reduce a reflection of the ultrasonic wave at the interface with respect to air and can increase the ultrasonic wave that enters the receiving devices R1-R4. In addition, the acoustic matching parts 12 are disposed at an outside of the piezoelectric elements 11, respectively, and thereby the piezoelectric elements 11 are invisible from the outside of the bumper 20. Thus, the acoustic matching parts 12 function as protection members for protecting the piezoelectric elements 11 from a foreign material and moisture. For example, the acoustic matching parts 12 are made of polycarbonate resin or polyetherimide resin. Each of the polycarbonate resin and the polyetherimide resin has an elasticity that is less affected by temperature. Thus, a wavelength of the ultrasonic wave transmitted through the acoustic matching parts 12 is less affected by temperature.

Each of the acoustic matching parts 12 has a width W that is less than or equal to a half wavelength of the ultrasonic wave transmitted in air. The acoustic matching parts 12 are arranged in such a manner that a distance Db between center portions of two adjacent acoustic matching parts 12 is substantially equal to the half wavelength of the ultrasonic wave. In addition, each of the acoustic matching parts 12 has a thickness T that is substantially quarter wavelength of the ultrasonic wave transmitted in the acoustic matching parts 12. For example, when a frequency of the ultrasonic wave is about 65 kHz, each of the acoustic matching parts 12 has the width W of about 2.6 mm and the thickness T about 5 mm.

When the thickness T of the acoustic matching parts 12 is substantially quarter wavelength of the ultrasonic wave, a standing wave is generated in the acoustic matching parts 12. Thereby, the ultrasonic wave entering the acoustic matching parts 12 and the ultrasonic wave reflected at interfaces between the acoustic matching parts 12 and the piezoelectric elements 11 are restricted from interfering with each other and reducing each other. Thus, the ultrasonic wave can be transmitted to the piezoelectric elements 11 efficiently. The material of the acoustic matching parts 12 is not limited to the resin. Alternatively, the acoustic matching parts 12 may be made of metal including aluminum, ceramic, or glass that satisfies the relationship of the acoustic impedances and the relationship between the wavelength and a dimension including the width W, the distance Db, and the thickness T. Each of the above-described materials has an environment resistance including a weather resistance similarly to the resin. The cross-sectional shape of the acoustic matching parts 12 is not limited to the approximately square shape. Alternatively, the cross-sectional shape of the acoustic matching parts 12 may be approximately circular shape.

The vibration-reducing member 13 is made of a material that has a smaller acoustic impedance and a higher attenuation constant compared with the acoustic matching parts 12. In addition, the vibration-reducing member 13 is made of a material having a small elasticity and a small density. For example, the vibration-reducing member 13 may be made of rubber, a resin having pore such as resin foam, or a sponge.

The vibration-reducing member 13 is provided between the acoustic matching parts 12 and between each of the acoustic matching parts 12 and the bumper 20. Thereby, the ultrasonic wave is reduced from transmitting from one of the acoustic matching parts 12 to the adjacent acoustic matching part 12. In addition, the ultrasonic wave is reduced from transmitting from the bumper 20 to the side surfaces 12*c* of the acoustic matching parts 12 through the attaching part 20*a*. Thus, a noise is reduced. Furthermore, when the vibration-reducing member 13 is made of a material having a small elasticity, the vibration-reducing member 13 has less effect on vibrations of the acoustic matching parts 12 due to the ultrasonic wave. Thus, an attenuation of the ultrasonic wave can be reduced.

The ultrasonic sensor 10 sends the ultrasonic wave from the sending device (not shown) or the first receiving device R1 and receives the ultrasonic wave reflected by an external object at the receiving surfaces 12*a* of the acoustic matching parts 12. The ultrasonic wave received by the receiving surfaces 12*a* is transmitted to the piezoelectric elements 11 through the acoustic matching parts 12, respectively. Then, the piezoelectric elements 11 detect the ultrasonic wave and convert into voltage signals. The piezoelectric elements 11 output the voltage signals to the ECU through the circuit device (not shown). The ECU executes the arithmetic processing. Thereby, the ultrasonic sensor 10 detects a location of the object, a distance to the object, a two-dimensional shape of the object, or a three-dimensional shape of the object.

Figure 2A:
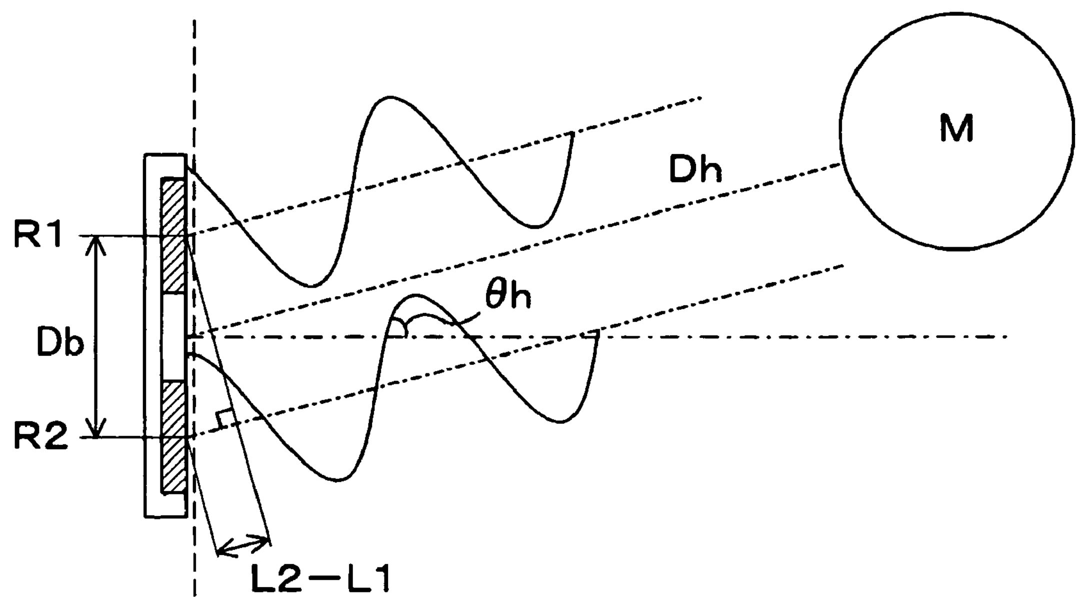
FIG. 2A is a schematic diagram showing a state where an ultrasonic wave reflected by an external object is detected by receiving devices.
Figure 2B:
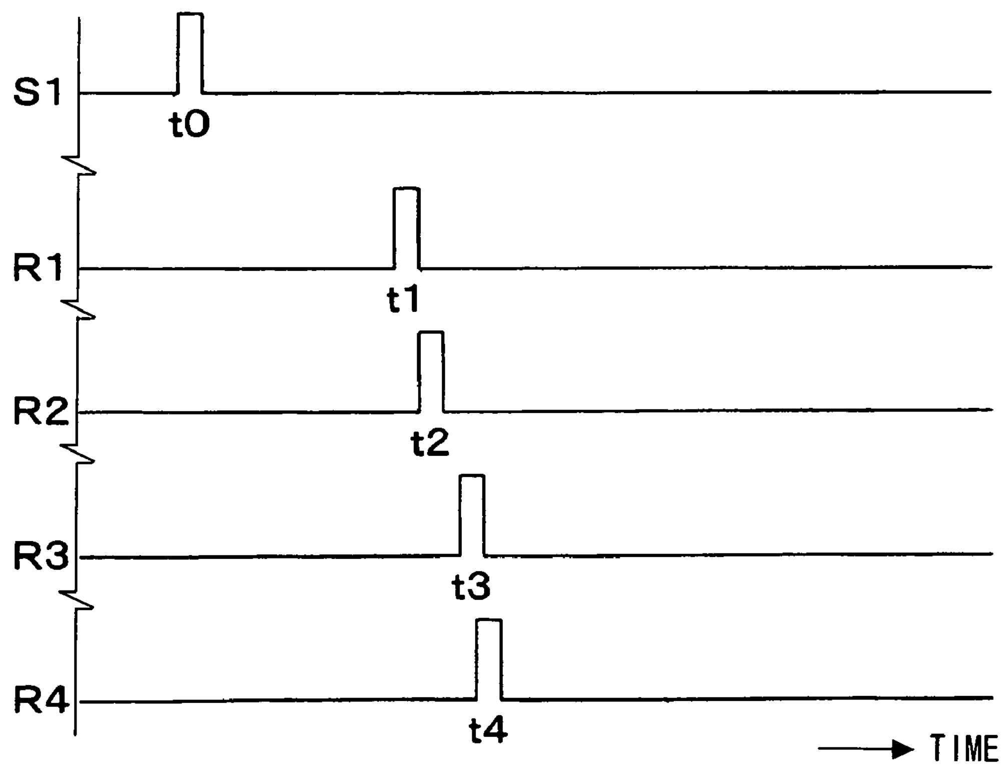
FIG. 2B is a timing chart showing detection signals of the receiving devices.

A method of detecting the three-dimensional shape of the object will now be described with reference to FIGS. 2A and 2B. In the present case, an obstacle M is located at a portion that is away from a front side of the vehicle at a distance Dh and at an angle of θh on a right side (on a side of the first receiving device R1) with respect to the front side of the vehicle, for example.

An ultrasonic wave sent from a sending device S1 (not shown) at time t0 is reflected by the obstacle M and is received by the first receiving device R1 and the second receiving device R2 at time t1 and time t2, respectively. Because the obstacle M is located on the right side with respect to the front side of the vehicle, a first distance L1 from the first receiving device R1 to the obstacle M is shorter than a second distance L2 from the second receiving device R2 to the obstacle M. Thus, time t1-t0 from when the ultrasonic wave is sent from the sending device till when the ultrasonic wave reflected by the obstacle M is received by the first receiving device R1 is shorter than time t2-t0 from when the ultrasonic wave is sent from the sending device till when the ultrasonic wave reflected by the obstacle M is received by the second receiving device R2. When the angle θh becomes large, the distance difference L2-L1 becomes large, and thereby the time difference t2-t1 becomes large. Thus, the angle θh can be calculated by using the time difference t2-t1. In addition, the average distance Dh from the first receiving device R1 and the second receiving device R2 to the obstacle M can be calculated by using an average of time t1-t0 and time t2-t0.

In a manner similar to the above-described method, an angle θv of the obstacle M on the up-and-down direction with respect to the ultrasonic sensor 10 and an average distance Dv from the first receiving device R1 and the third receiving device R3 to the obstacle M can be calculated by using times t1 and t3 at where the ultrasonic wave reflected by the obstacle M are detected by the first receiving device R1 and the third receiving device R3, respectively. Alternatively, the angle θv of the obstacle M on the up-and-down direction and an average distance from the first receiving device R2 and the fourth receiving device R4 to the obstacle M can be calculated by using times t2 and t4 at where the ultrasonic wave reflected by the obstacle M are detected by the second receiving device R2 and the fourth receiving device R4, respectively.

A distance and a direction of the obstacle M with respect to the ultrasonic sensor 10 can be calculated based on the distances Dh and Dv and the angles θh and θv. Thus, the three-dimensional shape of the obstacle M can be calculated based on the difference in time at where the ultrasonic wave reflected by the obstacle M is detected by the first to fourth receiving devices R1-R4, respectively. Alternatively, the three-dimensional shape of the obstacle M may be calculated based on a phase difference of the ultrasonic wave detected by the first to fourth receiving devices R1-R4, respectively.

In the ultrasonic sensor 10, each of the acoustic matching parts 12 has the width W that is less than or equal to the half wavelength of the ultrasonic wave transmitted in air. In addition, the acoustic matching parts 12 are arranged in such a manner that the distance Db between the center portions of two adjacent acoustic matching parts 12 is substantially equal to the half wavelength of the ultrasonic wave. In the present case, the time difference can be calculated based on the phase difference of the ultrasonic wave received by the receiving devices R1-R4 with a high degree of accuracy. Thus, the distance and the angle of the obstacle M with respect to the ultrasonic sensor 10 can be calculated with a high degree of accuracy. Even when the width W that is greater than the half wavelength of the ultrasonic wave transmitted in air, the three-dimensional shape of the object can be detected.

Figure 3A:
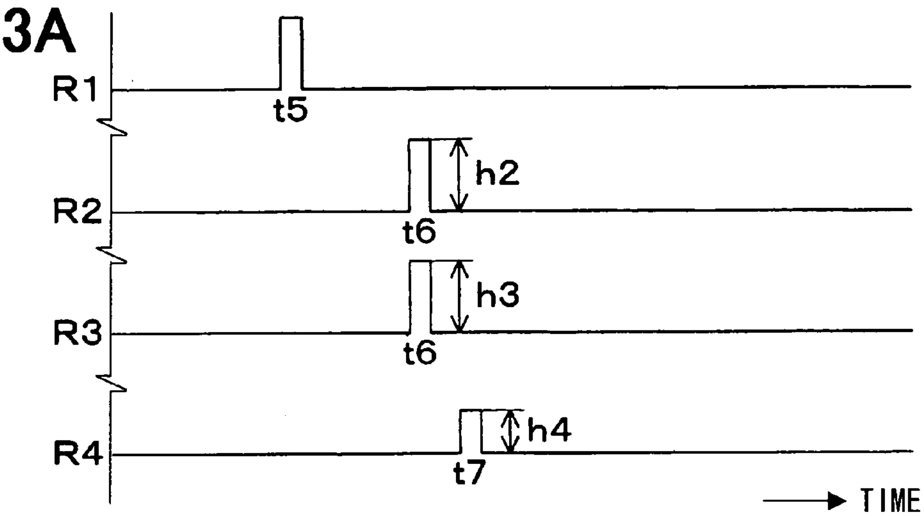
FIG. 3A is a timing chart of the detection signals in a case where the receiving devices are operated without malfunction.
Figure 3B:
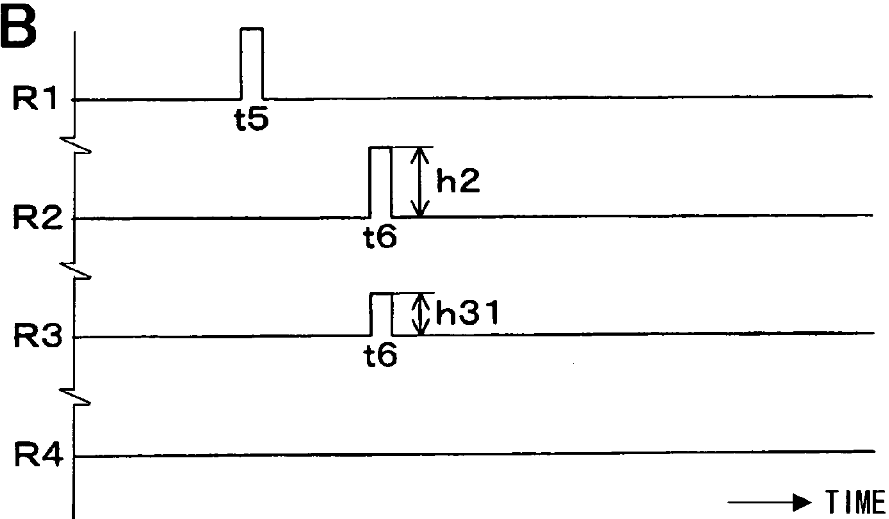
FIG. 3B and FIG. 3C are timing charts of the detection signals in a case where at least one of the receiving devices malfunctions.

A self diagnostic method of the ultrasonic sensor 10 will be described with reference to FIGS. 3A-3C. At first, the piezoelectric element 11 of the first receiving device R1, which is configured to be sendable and receivable, sends an ultrasonic wave to the acoustic matching part 12. The ultrasonic wave sent from the first receiving device R1 has an intensity higher than that of the ultrasonic wave reflected by the obstacle M, and can be transmitted through the vibration-reducing member 13. For example, the intensity of the ultrasonic wave sent from the first receiving device R1 is ten times higher than that of the ultrasonic wave reflected by the obstacle M. The ultrasonic wave sent from the acoustic matching part 12 of the first receiving device R1 to the vibration-reducing member 13 is transmitted to the acoustic matching parts 12 of the second to fourth receiving devices R2-R4.

The center portions of the second receiving device R2 and the third receiving device R3 are respectively away from the center portion of the first receiving device R1 at the distance Db. In addition, the center portion of the fourth receiving device R4 is away from the center portion of the first receiving device R1 at the distance $\sqrt{2}$ Db. Thus, when the second to fourth receiving devices R2-R4 are operated without malfunction, an ultrasonic wave sent from the first receiving device R1 at time t5 is detected by the second receiving device R2 and the third receiving device R2 at substantially same time t6 and is detected by the fourth receiving device R4 at time t7 that is later than time t6, as shown in FIG. 3A. The ultrasonic wave detected by the fourth receiving device R4 has transmitted through the vibration-reducing member 13 longer than the ultrasonic wave detected by the second receiving device R2 and the third receiving device R3. Thus, an intensity h4 of the detection signal of the fourth receiving device R4 is lower than an intensity h2 of the detection signal of the second receiving device R2 and an intensity h3 of the detection signal of the third receiving device R3. In the present case, the intensity h2 and the intensity h3 are substantially equal to each other.

In a case where one of the receiving devices R2-R4 is damaged and malfunctions, the detection signal of the damaged receiving device changes. For example, when the third receiving device R3 and the fourth receiving device R4 malfunction, an intensity h31 of the detection signal of the third receiving device R3 may be lower than the intensity h2 of the detection signal of the second receiving device R2, as shown in FIG. 3B. In addition, the fourth receiving device R4 may detect no signal. In this way, the ultrasonic sensor 10 can self-diagnose for detecting a receiving device having a trouble by comparing the intensities of the detection signals of the second to fourth receiving devices R2-R4 with those in a case where the second to fourth receiving devices R2-R4 are operated without malfunction. Thus, the ultrasonic sensor 10 can detect a malfunction of a receiving device without sending an ultrasonic wave toward an external object and detecting the ultrasonic wave reflected by the external object.

Figure 3C:
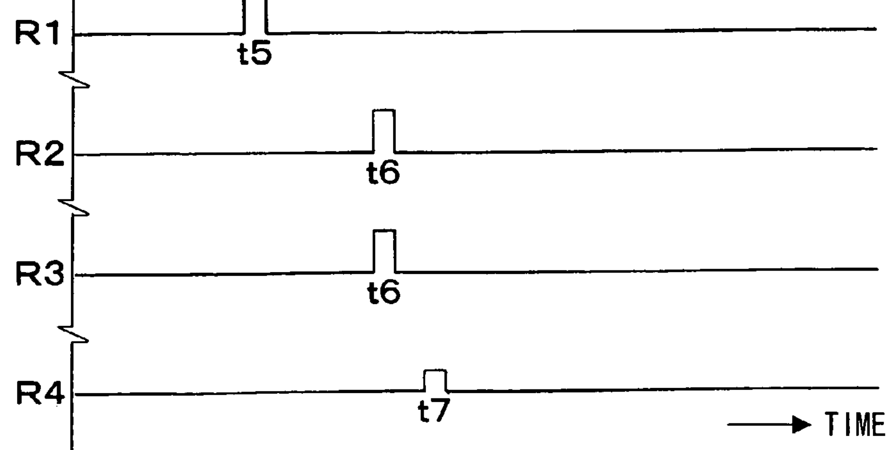
Figure 4:
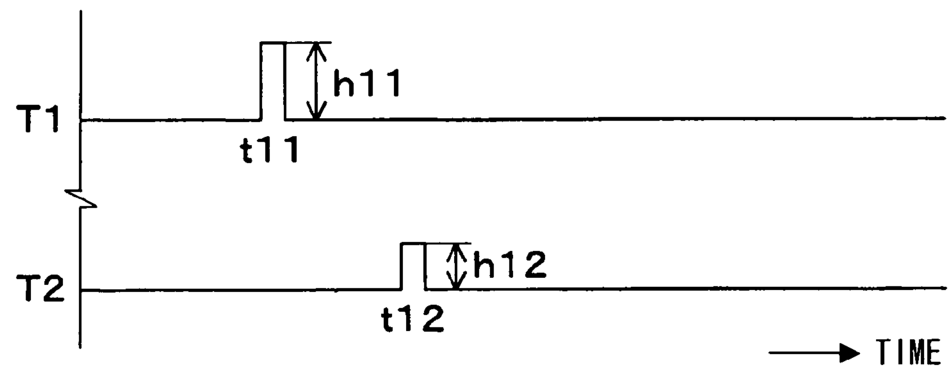
FIG. 4 is a timing chart showing a temperature dependency of the detection signals.

In a case where the intensities of the detection signals of all the second to fourth receiving devices R2-R4 are reduced, as shown in FIG. 3C, or in a case where the all the second to fourth receiving devices R2-R4 detect no signal, all the second to fourth receiving devices R2-R4 malfunction or the first receiving device R1 malfunctions. When the second receiving device R2 is also configured to be sendable, the ultrasonic sensor 10 can detect which receiving device malfunctions by comparing the detection signals of the receiving devices R2-R4 in a case where the first receiving device R1 sends the ultrasonic wave with the detection signals of receiving devices R1, R3, and R4 in a case where the second receiving device R2 sends the ultrasonic wave.

For example, if the ultrasonic sensor 10 detects that the fourth receiving device R4 malfunctions in the self diagnosis, the ultrasonic sensor 10 blocks the detection signal from the fourth receiving device R4 and detects the obstacle M by using the receiving devices R1-R3. Thereby, the ultrasonic sensor 10 can have a fail safe function, and a reliability of the ultrasonic sensor 10 can be improved.

In addition, when the ultrasonic sensor 10 includes a plurality of receiving devices that is sendable, for example, the first receiving device R1 and the second receiving device R2, the ultrasonic sensor 10 can detect a variation in the intensities of the detection signals by comparing the intensities of the detection signals of the receiving devices R1-R4. The ultrasonic sensor 10 can correct a sensitivity thereof by detecting the variation with respect to the intensities of the detection signals of the receiving devices R1-R4 that are operated without malfunction and controlling a gain of the detection signals by the circuit device.

For example, the ultrasonic wave sent from the receiving device may have a frequency same as the intensity of the ultrasonic wave used for detecting the obstacle M. That is, the ultrasonic wave sent from the receiving device may have a resonant frequency of the acoustic matching parts 12. In the present case, a vibration becomes large, and thereby the ultrasonic sensor 10 can self diagnose with a high degree of accuracy. Furthermore, when the acoustic matching parts 12 are deformed, for example, by an object coming from an outside of the ultrasonic sensor 10, the resonant frequency changes, and thereby the intensities of the detection signals drastically change. Thus, the ultrasonic sensor 10 can detect the deformation of the acoustic matching parts 12.

In the ultrasonic sensor 10, the ECU can estimate temperature based on temperature dependencies of properties of components through which the ultrasonic wave transmits. Then, the ultrasonic sensor 10 can be corrected for temperature by using the estimated temperature. A method of detecting temperature will be described. When the surrounding temperature of the ultrasonic sensor 10 increases, the elasticity of the acoustic matching parts 12 and the elasticity of the vibration-reducing member 13 are reduced. Thereby, acoustic velocities of the ultrasonic wave transmitted through the acoustic matching parts 12 and the vibration-reducing member 13 are respectively reduced. Thus, detecting times at which the ultrasonic wave is detected by the reducing devices R1-R4 shift to a longer side. In addition, an attenuation of the ultrasonic wave due to the vibration-reducing member 13 increases, and thereby the intensities of the detection signals are reduced.

For example, when a surrounding temperature T2 is higher than a predetermined temperature T1, an intensity of a detection signal is reduced from an intensity h11 to an intensity h12. In addition, a detecting time shifts to time t11 to time t12. The ultrasonic sensor 10 can estimate the surrounding temperature T2 based on the temperature properties of the acoustic matching parts 12 and the vibration-reducing member 13 and one of the an attenuation ratio h12/h11 and a shift amount of the detecting time t12-t11. In addition, the ultrasonic sensor 10 can change the frequency of the ultrasonic wave sent from the sending device based on the estimated temperature T2. Furthermore, the ultrasonic sensor 10 can correct the sensitivity thereof based on the estimated temperature T2 by using the circuit device or the ECU.

Figure 5:
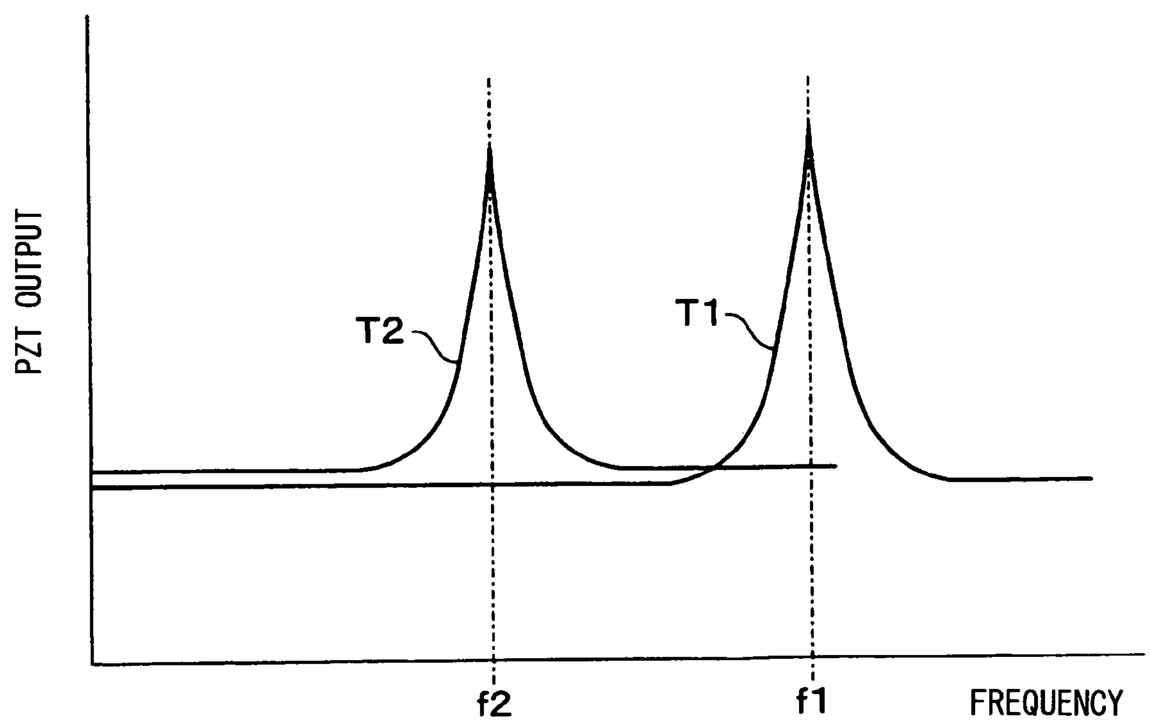
FIG. 5 is a graph showing a temperature dependency of a resonant frequency of acoustic matching parts.

Alternatively, the surrounding temperature T2 can be estimated based on the variation in the resonant frequency of the acoustic matching parts 12. As shown in FIG. 5, when the frequency of the ultrasonic wave sent from the first receiving device R1 is swept at the predetermined temperature T1, the acoustic matching part 12 of the second receiving device R1 resonates at a frequency f1. Thus, the intensity of the detection signal of the second receiving device increases at the frequency f1. At the surrounding temperature T2, the elasticity of the acoustic matching part 12 is reduced. Thus, the thickness of the acoustic matching part 12 increases and the resonant frequency becomes frequency f2 that is lower than the frequency f1. The ultrasonic sensor 10 can estimate the surrounding temperature T2 based on the temperature dependency of the resonant frequency. For example, a swept frequency of the ultrasonic wave may be in a ranged from 0.5 times to 2 times of an assumed resonant frequency f2.

The number of the receiving devices and the arrangement of the reducing devices may be changed. For example, the receiving device may be arranged concentrically. Alternatively, only two reducing devices R1 and R2 may be provided to detect the two-dimensional shape on a right-and-left direction. When the two receiving devices R1 and R2 are used, a threshold value of the detection signal with respect to the sending ultrasonic wave may be set. In the present case, the ultrasonic sensor 10 can determine that the one of the receiving devices R1 and R2 malfunctions when the detection signal is lower than the threshold value.

In the ultrasonic sensor 10, at least one of the receiving devices R1-R4, for example, the first receiving device R1 is configured to be sendable. The ultrasonic wave sent from the first receiving device R1 is transmitted to the receiving devices R2-R4 through the vibration-reducing member 13. Then, the ultrasonic sensor 10 determines whether each of the receiving devices R2-R4 is operated without malfunction based on the detection signals of the receiving devices R2-R4. Thus, the ultrasonic sensor 10 can detect a malfunction of the receiving devices R2-R4 without sending an ultrasonic wave toward an external object and detecting the ultrasonic wave reflected by the external object. As a result, the ultrasonic sensor 10 can self diagnose at a desired time. Thus, the reliability of the ultrasonic sensor 10 can be improved.

Each of the acoustic matching parts 12 is configured in such a manner that the standing wave is generated therein by the ultrasonic wave received at the receiving surface 12*a*. Thereby, the ultrasonic wave entering the acoustic matching parts 12 and the ultrasonic wave reflected at interfaces between the acoustic matching parts 12 and the piezoelectric elements 11 are restricted from interfering with each other and reducing each other. Thus, the ultrasonic wave can be transmitted to the piezoelectric elements 11 efficiently. As a result, the sensitivity of the ultrasonic sensor can be improved.

In addition, because the frequency of the ultrasonic wave sent from the first receiving device R1 is the resonant frequency of the acoustic matching parts 12, the acoustic pressure can be increased. Thereby, the intensities of the detection signal of the receiving devices R2-R4 increases, and the ultrasonic sensor 10 can self diagnose with a high degree of accuracy.

The property of the components through which the ultrasonic wave transmits, for example, the property of the acoustic matching parts 12 changes with temperature. The detecting times of the detection signals and the intensities of the detection signals change in accordance with the change of the properties. The surrounding temperature of the ultrasonic sensor 10 can be estimated based on the detecting times of the detection signals or the intensities of the detection signal by using the temperature dependency. In addition, the resonant frequency of the acoustic matching parts 12 or the intensities of the detection signals at the resonant frequency changes with temperature. Thus, the surrounding temperature of the ultrasonic sensor 10 can be estimated based on the resonant frequency of the acoustic matching parts 12 or the intensities of the detection signals at the resonant frequency.

For example, the acoustic matching parts 12 are made of polycarbonate resin or polyetherimide resin. The elasticity of the polycarbonate resin and the elasticity of the polyetherimide resin are less affected by temperature. Thus, the wavelength of the ultrasonic wave is reduced from changing with temperature, and thereby standing wave can be stably generated. Furthermore, when the piezoelectric elements 11 are made of the PZT having a large piezoelectric constant, the ultrasonic sensor 10 can detect the ultrasonic wave having a small acoustic pressure. Thus, the sensitivity of the ultrasonic sensor 10 can be improved.

When the width W of the acoustic matching parts 12 is less than a half wavelength of the ultrasonic wave transmitted in air, the plurality of receiving devices can be arranged in such a manner that the center portions of the receiving devices are away from each other at the distance Db that is substantially equal to the half wavelength of the ultrasonic wave transmitted in air. As a result, the ultrasonic sensor 10 can detect with a high degree of accuracy.

Second Embodiment

Figure 6:
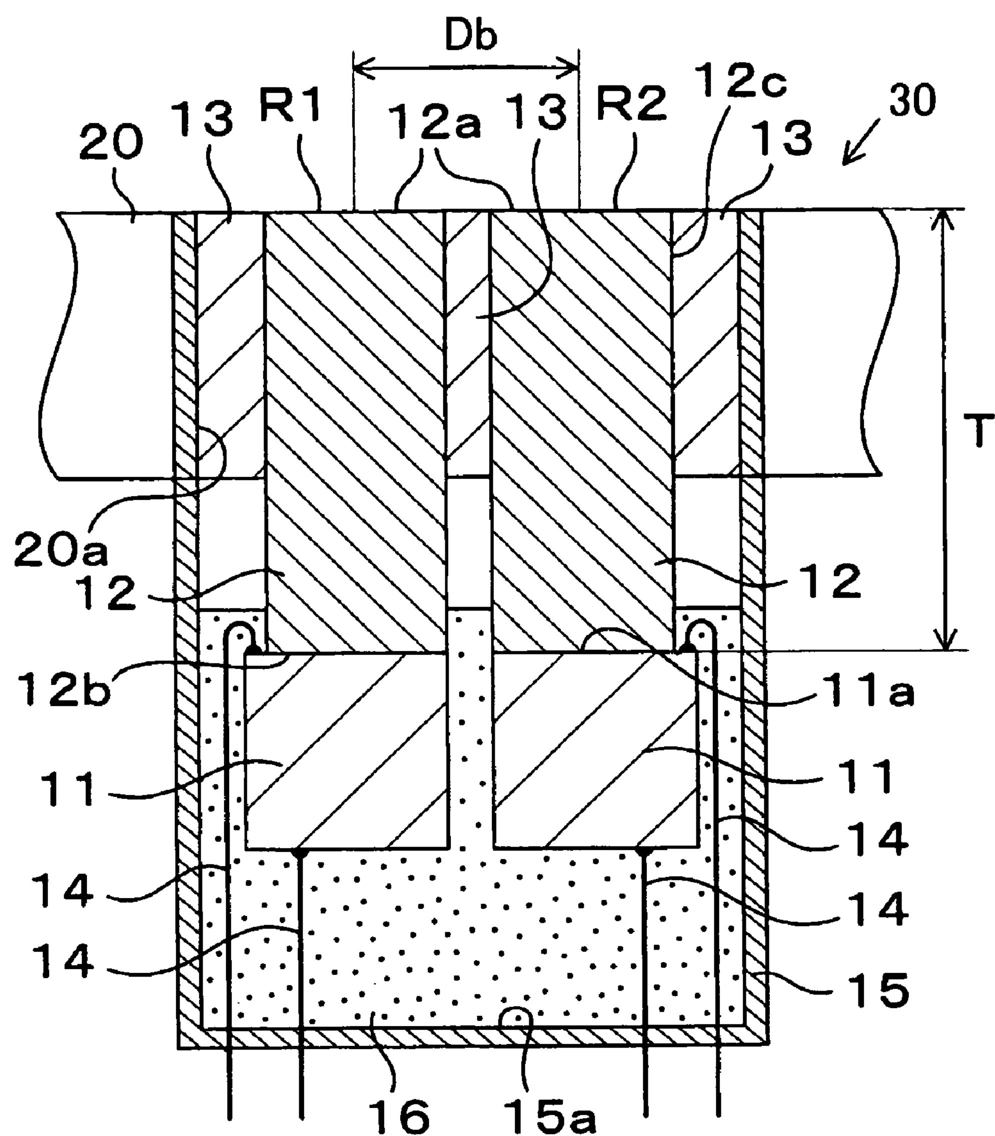
FIG. 6 is a cross-sectional view showing an ultrasonic sensor according to a second embodiment of the invention.
Figure 7:
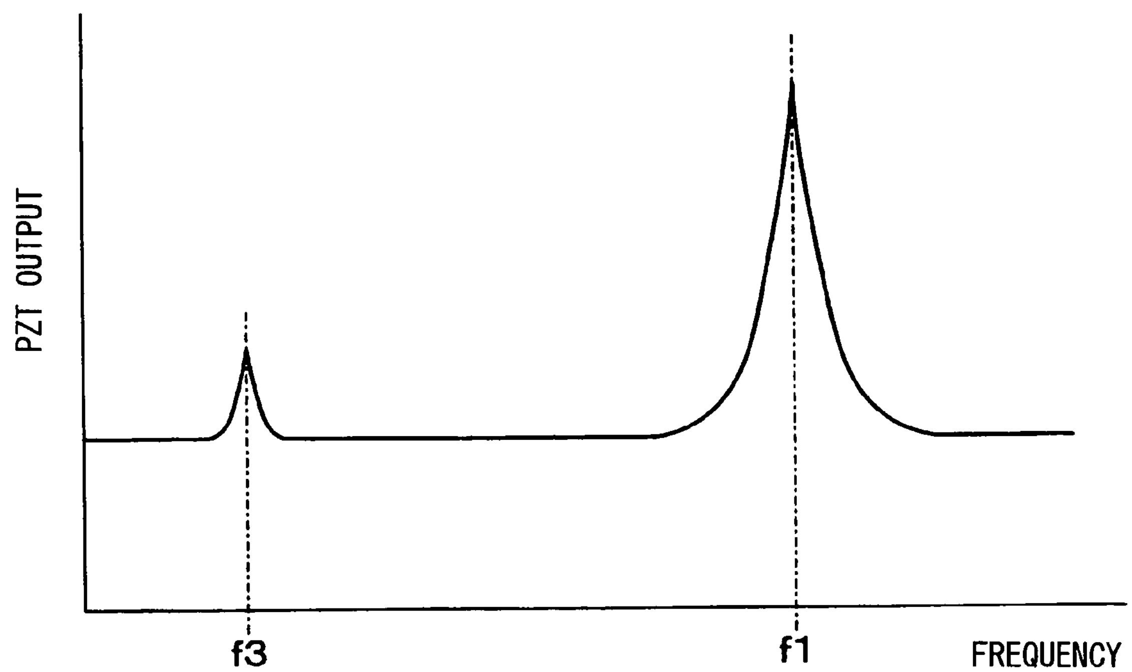
FIG. 7 is a graph showing resonant signals of the acoustic matching parts and the sealing member.

An ultrasonic sensor 30 according to a second embodiment of the invention will be described with reference to FIGS. 6 and 7. In the ultrasonic sensor 30, a sealing member 16 is provided at a bottom part 15*a* of the casing 15 so as to cover the piezoelectric elements 11. The sealing member 16 protects the piezoelectric elements 11 from moisture and reduces a stress applied to the piezoelectric elements 11 due to the vibration. The sealing member 16 is made of a material having a low acoustic impedance. In addition, the sealing member 16 is made of a material having a low elasticity so that the vibrations of the acoustic matching parts 12 are not affected by the sealing member 16. For example, the sealing member 16 is made of silicon rubber, urethane foam, or gel. For example, the elasticity of the sealing member 16 is less than or equal to 10 Mpa.

The ultrasonic sensor 30 can self diagnose by using the sealing member 16 as a transmission medium. Specifically, the ultrasonic wave sent from the first receiving device R1 is transmitted to the receiving devices R2-R4 through the sealing member 16. The ultrasonic sensor 30 can self diagnose by using the detection signals of the ultrasonic waves transmitted through the sealing member 16 in a manner similar to the self diagnostic method of the ultrasonic sensor 10.

A physical property of the sealing member 16 changes in accordance with temperature. Thus, the ultrasonic sensor 30 can estimate temperature in a manner similar to the first embodiment. In a case where the ultrasonic sensor 30 estimate temperature by sweeping the frequency of the ultrasonic wave sent from the first receiving device R1, the frequency may be swept in a range from about 0.3 times to 3 times. The elasticity of the sealing member 16 is lower than that of the acoustic matching parts 12. Thus, as shown in FIG. 7, a resonant frequency f3 of the sealing member 16 is lower than the resonant frequency f2 of the acoustic matching parts 12. In addition, the intensity of the detection signal of the second receiving device R2 at the resonant frequency f3 of the sealing member 16 is lower than the intensity of the detection signal of the second receiving device R2 at the resonant frequency f2 of the acoustic matching parts 12. In this way, because the resonant frequency f3 of the sealing member 16 is different from the resonant frequency f2 of the acoustic matching parts 12, the resonant frequency f3 can be discriminated from the resonant frequency f2. In addition, the ultrasonic sensor 30 can estimate temperature with high degree of accuracy by using the temperature dependencies of the resonant frequency f2 of the acoustic matching parts 12 and the resonant frequency f3 of the sealing member 16.

In the ultrasonic sensor 30, at least one of the receiving devices R1-R4, for example, the first receiving device R1 is configured to be sendable. The ultrasonic wave sent from the first receiving device R1 is transmitted to the receiving devices R2-R4 through the sealing member 16. Then, the ultrasonic sensor 30 determines whether each of the receiving devices R2-R4 is operated without malfunction based on the detection signals of the receiving devices R2-R4. Thus, the ultrasonic sensor 30 can detect a malfunction of the receiving devices R2-R4 without sending an ultrasonic wave toward an external object and detecting the ultrasonic wave reflected by the external object. As a result, the ultrasonic sensor 30 can self diagnose at a desired time. Thus, the reliability of the ultrasonic sensor 30 can be improved.

Third Embodiment

Figure 8:
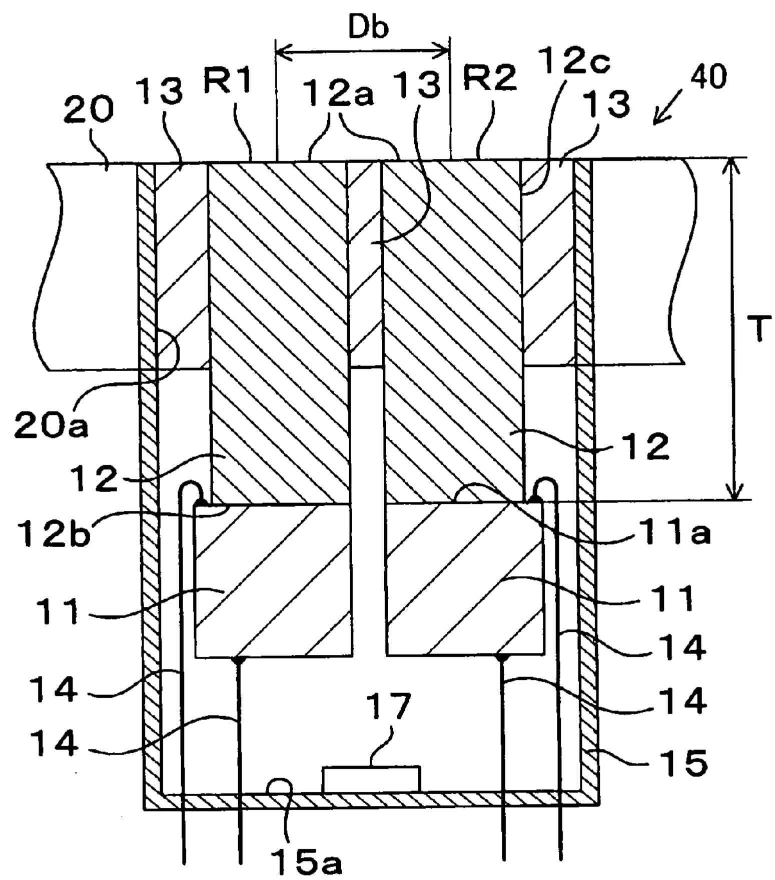
FIG. 8 is a cross-sectional view showing an ultrasonic sensor according to a third embodiment of the invention.

An ultrasonic sensor 40 according to a third embodiment of the invention will be described with reference to FIG. 8. In the ultrasonic sensor 40, a sending device 17 for a self diagnosis is disposed at the bottom part 15*a* of the casing 15. The sending device 17 is made of a piezoelectric element, for example. The sending device 17 has a sending surface from which an ultrasonic wave is sent. The sending device 17 is arranged in such a manner that distances from the sending surface to the receiving devices R1-R4 are substantially equal to each other. When the ultrasonic sensor 40 self-diagnoses, the sending device 17 sends the ultrasonic wave toward the receiving devices R1-R4. The ultrasonic wave output from the sending device 17 is transmitted to each of the piezoelectric elements 11 or each of the acoustic matching parts 12. The distances from the sending surface to the receiving devices R1-R4 are substantially equal to each other. Thus, when the receiving devices R1-R4 are operated without malfunction, the detecting times and the intensities of the detection signals of the receiving devices R1-R4 are substantially equal to each other. When the detection signal of the one receiving device decreases, the ultrasonic sensor 40 detects that the one receiving device malfunctions. Because the ultrasonic sensor 40 includes the sending device 17 for the self diagnosis, the receiving devices R1-R4 are not required to be sendable. In addition, the ultrasonic sensor 40 can diagnose the receiving devices R1-R4 at the same time. In addition, the ultrasonic sensor 40 can estimate temperature based on the detection signals of the receiving devices R1-R4 in a manner similar to the first embodiment and the second embodiment.

The sending device 17 may be sealed by the sealing member 16 with the piezoelectric elements 11. In the present case, the ultrasonic wave output from the sending device 17 is transmitted to the receiving devices R1-R4 through the sealing member 16. Thus, the intensities of the detection signals increase compared with a case where the sealing member 16 is not provided and the ultrasonic wave is transmitted in air.

The sending device 17 is not required to be disposed at an equal distance from the receiving devices R1-R4 as long as the sending device 17 is disposed on a side of the piezoelectric elements 11 with respect to the receiving surfaces 12*a*. For example, the sending device 17 is disposed on an inner surface of the casing 15 other than the bottom part 15*a*. In the present case, the detecting times and the intensities of the detection signals are different from each other. However, the ultrasonic sensor 40 can diagnose the receiving devices R1-R4 by comparing the detecting times and the intensities of the detection signals with those in a case where the receiving devices R1-R4 are operated without malfunction. In addition, when the sending device 17 is not required to be disposed at an equal distance from the receiving devices R1-R4, the sending device 17 can be arranged more freely and thereby, the ultrasonic sensor 40 can be small.

In the ultrasonic sensor 40, the sending device 17 is disposed on the side of the receiving devices R1-R4 with respect to the receiving surfaces 12*a*. The ultrasonic wave sent from the sending device 17 is transmitted to the receiving devices R1-R4. Then, the ultrasonic sensor 40 determines whether each of the receiving devices R1-R4 is operated without malfunction based on the detection signals of the receiving devices R1-R4. Thus, the ultrasonic sensor 40 can detect a malfunction of the receiving devices R1-R4 without sending an ultrasonic wave toward an external object and detecting the ultrasonic wave reflected by the external object. As a result, the ultrasonic sensor 10 can self diagnose at a desired time. Thus, the reliability of the ultrasonic sensor 40 can be improved. Furthermore, because the ultrasonic sensor 40 includes the sending device 17 for the self diagnosis, the receiving devices R1-R4 are not required to be sendable. In addition, the ultrasonic sensor 40 can diagnose the receiving devices R1-R4 at the same time.

In a case where the sending device 17 is disposed at an equal distance from the receiving devices R1-R4, the detecting times and the intensities of the detection signals of the receiving devices R1-R4 are equal to each other when the receiving devices R1-R4 are operated without malfunction. Thus, the ultrasonic sensor 40 can detect which receiving device malfunctions by comparing the detection signals.

Other Embodiments

Although the present invention has been fully described in connection with the preferred embodiments thereof with reference to the accompanying drawings, it is to be noted that various changes and modifications will become apparent to those skilled in the art.

Each of the ultrasonic sensors 10, 30, and 40 may be also attached to a portion of the vehicle 60 other than the bumper 20. For example, each of the ultrasonic sensors 10, 30, and 40 may be attached at a head-lamp cover 21. In the present case, the ultrasonic wave reflected by the obstacle is reduced from being blocked by a portion of the vehicle 60. Thus, the ultrasonic sensors 10, 30, and 40 can be suitably used for an obstacle sensor. Alternatively, each of the ultrasonic sensors 10, 30, and 40 may be attached to a direction-indicator cover 22 or a side mirror 23 when each of the ultrasonic sensors 10, 30, and 40 is used as an obstacle sensor on a side direction of the vehicle 60. Alternatively, each of the ultrasonic sensors 10, 30, and 40 may be attracted to a rear-lamp cover 24 or a back-lamp cover 25 when each of the ultrasonic sensors 10, 30, and 40 is used as an obstacle sensor on a rear side of the vehicle 60.

The acoustic matching parts 12 of the receiving devices R1-R4 may be made of materials different from each other. For example, the acoustic matching parts 12 of the receiving devices R1 and R2 may be made of a polycarbonate resin and the acoustic matching parts 12 of the receiving devices R3 and R4 are made of an aluminum alloy. Temperature dependencies of physical property, for example, temperature dependencies of elasticity of the polycarbonate resin and the aluminum alloy are different from each other. Thus, the each of the ultrasonic sensors 10, 30, and 40 can estimate temperature with high degree of accuracy by using the temperature dependencies of both of the polycarbonate and the aluminum alloy.

Such changes and modifications are to be understood as being within the scope of the present invention as defined by the appended claims.

What is claimed is:

1. A self diagnostic method of an ultrasonic sensor, comprising:

sending an ultrasonic wave from a first receiving device that is configured to be sendable and receivable;

transmitting the ultrasonic wave through a vibration-reducing member;

detecting the ultrasonic wave by a second receiving device; and determining whether the second receiving device is operated without malfunction based on a detection signal of the second receiving device, wherein:

each of the receiving devices includes a detecting element and an acoustic matching part;

each of the detecting elements has a first acoustic impedance and is configured to detect an ultrasonic wave that is sent from a sending device and that is reflected by an external object;

each of the acoustic matching parts has a second acoustic impedance and has a receiving surface and an attaching surface;

each of the receiving surfaces is exposed to an outside for detecting the ultrasonic wave reflected by the external object;

each of the attaching surfaces opposes the receiving surface and is attached to the detecting element for transmitting the ultrasonic wave received by the receiving surface to the detecting element;

the second acoustic impedance is larger than an acoustic impedance of air and is less than the first acoustic impedance; and the acoustic matching part of the first receiving device and the acoustic matching part of the second receiving device are arranged through the vibration-reducing member for reducing a transmission of a vibration between the acoustic matching parts.

2. The self diagnostic method according to claim 1, wherein each of the acoustic matching parts is configured in such a manner that a standing wave is generated therein by the ultrasonic wave received at the receiving surface.

3. The self diagnostic method according to claim 1, wherein the ultrasonic wave sent from the first receiving device has a resonant frequency of the acoustic matching parts.

4. A self diagnostic method of an ultrasonic sensor, comprising:

sending an ultrasonic wave from a first receiving device that is configured to be sendable and receivable;

transmitting the ultrasonic wave through a sealing member;

detecting the ultrasonic wave by a second receiving device; and determining whether the second receiving device is operated without malfunction based on a detection signal of the second receiving device, wherein:

each of the receiving devices includes a detecting element and an acoustic matching part;

each of the detecting elements has a first acoustic impedance and is configured to detect an ultrasonic wave that is sent from a sending device and that is reflected by an external object;

each of the acoustic matching parts has a second acoustic impedance and has a receiving surface and an attaching surface;

each of the receiving surfaces is exposed to an outside for detecting the ultrasonic wave reflected by the external object;

each of the attaching surfaces opposes the receiving surface and is attached to the detecting element for transmitting the ultrasonic wave received by the receiving surface to the detecting element;

the second acoustic impedance is larger than an acoustic impedance of air and is less than the first acoustic impedance;

the acoustic matching part of the first receiving device and the acoustic matching part of the second receiving device are arranged through a vibration-reducing member for reducing a transmission of a vibration between the acoustic matching parts; and the detecting element of the first receiving device and the detecting element of the second receiving device are sealed by the sealing member.

5. The self diagnostic method according to claim 1, further comprising estimating a temperature of the ultrasonic sensor based on one of a time at which the second receiving device detects the ultrasonic wave sent from the first receiving device and an intensity of the detection signal of the second receiving device.

6. The self diagnostic method according to claim 1, further comprising:

sweeping a frequency of the ultrasonic wave sent from the first receiving device; and estimating a temperature of the ultrasonic sensor based on one of a resonant frequency of the acoustic matching part of the second receiving device and an intensity of the detection signal of the second receiving device in a case where the first receiving device sends the ultrasonic wave having the resonant frequency.

7. The self diagnostic method according to claim 1, wherein the acoustic matching parts are arranged in such a manner that center portions of the acoustic matching parts are away from each other at a distance that is substantially equal to a half wavelength of the ultrasonic wave transmitted in air.

8. The self diagnostic method according to claim 1, wherein the acoustic matching parts are made of one of a polycarbonate resin and a polyetherimide.

9. The self diagnostic method according to claim 1, wherein the detecting elements are made of a lead zirconate titanate.

10. The self diagnostic method according to claim 1, wherein the ultrasonic sensor is disposed at one of a head-lamp cover, a rear-lamp cover, a direction-indicator cover, a back-lamp cover, a door mirror, and a bumper of a vehicle.

11. The self diagnostic method according to claim 1, wherein:

the ultrasonic wave sent from the first receiving device has a first intensity; and the ultrasonic wave sent from the sending device has a second intensity that is less than the first intensity.

* * * * *